United States Patent [19]

Mueller

[11] Patent Number: 5,011,275

[45] Date of Patent: Apr. 30, 1991

[54] DIMETHYLACRYLAMIDE-COPOLYMER HYDROGELS WITH HIGH OXYGEN PERMEABILITY

[75] Inventor: Karl F. Mueller, New York, N.Y.

[73] Assignee: Ciba Geigy Corporation, Ardsley, N.Y.

[21] Appl. No.: 549,528

[22] Filed: Jul. 6, 1990

Related U.S. Application Data

[60] Division of Ser. No. 356,801, May 23, 1989, Pat. No. 4,954,587, which is a continuation-in-part of Ser. No. 215,101, Jul. 5, 1988, abandoned.

[51] Int. Cl.$^5$ ............................................. G02C 7/04
[52] U.S. Cl. ................................. 351/160 H; 623/6; 604/289; 604/890.1; 128/155
[58] Field of Search ................... 351/160 H; 623/6; 604/289, 890.1; 128/155

[56] References Cited

U.S. PATENT DOCUMENTS

| | | | |
|---|---|---|---|
| 2,834,763 | 5/1958 | Halpern et al. | 526/245 |
| 3,118,161 | 3/1963 | Cramton | 15/159 |
| 3,403,070 | 1/1964 | Lewis, Jr. | 161/175 |
| 3,411,979 | 8/1965 | Lewis, Jr. | 161/178 |
| 4,010,308 | 6/1975 | Wiczer | 428/372 |

FOREIGN PATENT DOCUMENTS

| | | | |
|---|---|---|---|
| 58-113932 | 7/1983 | Japan | 526/245 |
| 59-152909 | 8/1984 | Japan | 526/245 |

*Primary Examiner*—Joseph L. Schofer
*Assistant Examiner*—N. Sarofim
*Attorney, Agent, or Firm*—Luther A. R. Hall

[57] ABSTRACT

The invention describes polymers which are obtained by copolymerization of 15-85 wt % N,N-dimethylacrylamide with about 15-85% of a fluorinated monomer such as perfluoroalkyl-alkylene acrylate or methacrylate with from 3 to 25 fluorine atoms and optionally, 0-50 wt % other acrylates or methacrylates and 0-20 wt %, but not more than 5 mol % of a polyvinyl functional crosslinking agent. These polymers are machinable in the dry state and form clear hydrogels with about 25-75 wt % water content and which possess oxygen-permeabilities 3-7 times higher than conventional hydrogels of similar water content. In the absence of crosslinking, the novel polymers are plasticized by water, forming clear hydroplastics with 30-70 wt % water content. The crosslinked polymers are especially useful for fabricating contact lenses for extended wear by either cutting and polishing a xerogel button, or by spin casting or direct molding in bulk or in solution.

14 Claims, No Drawings

DIMETHYLACRYLAMIDE-COPOLYMER HYDROGELS WITH HIGH OXYGEN PERMEABILITY

This is a divisional of application Ser. No. 356,801 filed on May 23, 1989 now U.S. Pat. No. 4,954,587, which is a continuation-in-part of Ser. No. 215,101 filed on July 5, 1988 now abandoned.

BACKGROUND OF THE INVENTION

Hydrogels and their use as contact lenses have been known since at least Wichterle et. al. published U.S. Pat. No. 3,220,960, which discloses sparingly crosslinked, hydrated poly(hydroxyalkyl methacrylate), typified by poly(2-hydroxyethyl methacrylate) (poly-HEMA) with a water content of about 39%.

Poly-HEMA became the standard material for hydrogel contact lenses since it is hard enough to be easily fabricated by machining and polishing in the dry state, yet soft and comfortable to wear in the water swollen state.

In subsequent developments other hydrophilic monomers were used, most commonly N-vinyl-pyrrolidone (NVP) copolymers with methyl methacrylate (MMA) or other "high Tg" methacrylates. With this system, hydrogels with water contents up to 80% can be prepared. Dimethylacrylamide copolymers provide similar properties and have been described as well.

The oxygen transmissibility of such conventional hydrogel contact lenses is determined by their water content and thickness and can be improved by increasing the water content or by decreasing thickness. Both strategies have been used to increase $O_2$-permeability and to make extended-wear contact lenses, but both strategies lead to lenses with insufficient strength which are easily damaged. It is highly desirable to have a hydrogel soft lens with the same or similar good mechanical properties and as comfortable to wear as poly-HEMA, yet with substantially higher oxygen permeability. This can now be achieved by incorporation of either siloxane groups or fluorinated groups into the polymer compositions.

It would be especially desirable to have highly fluorinated hydrogels since, while siloxane groups give slightly higher oxygen permeability, fluorinated groups allow the manufacture of polymers with higher dry hardness and therefore better machinability while at the same time reducing lipophilicity and deposit formation on the hydrated polymer.

Among prior art compositions consisting of fluorinated hydrogels the following patents are relevant:

U.S. Pat. Nos. 4,433,111 and 4,493,910 describe hydrogels and contact lenses obtained by copolymerization of 20–40 mol % substituted or unsubstituted acrylamide or methacrylamide; 25–55 mol % N-vinylpyrrolidone (NVP); 5–20% mol hydroxy-alkyl(meth)-acrylate; 1–10 mol % (meth)-acrylic acid, and 1–9 mol % of a perfluoroalkyl-alkylene(meth)-acrylate; the perfluoroalkyl groups act to reduce protein deposition.

U.S. Pat. No. 4,640,965 describes hydrogels and contact lenses obtained by copolymerization of hydroxyfluoroalkylstyrene (5–60%, by weight), with hydroxyalkyl (meth)-acrylates or N-vinylpyrrolidone (40–95%, by weight); the hydroxy group is necessary to attain the required compatibility.

U.S. Pat. No. 4,638,040 describes the synthesis of 1,3-bis(trifluoro-acetoxy)propyl-2-methacrylate polymers and their use as hydrogel-contact lens materials and ocular implants after hydrolysis.

U.S. Pat. No. 4,650,843 describes hydrogel contact lens materials consisting essentially of copolymers of 50-95% (by weight) of 2-hydroxyethyl-methacrylate and 5-35% (by weight) of fluorinated methacrylates with up to 5 F-atoms.

In all these cases the range of clear compositions is very limited; the commercially available fluorinated (meth)acrylates can be incorporated in only relatively small amounts; alternatively, complicated, for instance hydroxylated F-monomers have to specially be synthesized to achieve better solubility in NVP or HEMA (U.S. Pat. No. 4,640,965). It has now unexpectedly been discovered that N,N-dimethylacrylamide when used as comonomer with fluorine-containing monomers gives clear copolymers within a wide range of possible compositions. This has been especially surprising since N-vinyl pyrrolidone (NVP), which has a solubility parameter, polarity and hydrogen-bonding capacity very similar to dimethylacrylamide (DMA), does not give clear compatible mixtures under the same conditions. [The solubility parameters $(cal/cm^3)^{\frac{1}{2}}$ for the analogous saturated molecules are: N,N-dimethylacetamide, $C_4H_9ON$: 10.8, moderate H-bonding; N-methylpyrrolidone, $C_5H_9ON$; 11.3, also moderately H-bonding.] In addition, the Copolymerization between DMA and acrylates and methacrylates in general proceeds much smoother because of more favorable reactivity-ratios, leading to a more random copolymer structure for DMA-copolymers than for NVP-copolymers. This, together with the good compatibility of DMA with fluorinated (meth)acrylates allows synthesis of highly $O_2$-permeable hydrogels which are harder than the corresponding silicone-hydrogel copolymers and, because of the oleophobic nature of fluorinated groups, more resistant to soiling and deposit formation.

Crosslinked dimethylacrylamide copolymers with other acrylic or methacrylic monomers and their use as conventional hydrogel-soft contact lenses are described in U.S. Pat. Nos. 4,328,148, 4,328,428 and 4,388,436.

Among silicone containing hydrogels of the prior art, U.S. Pat. Nos. 4,139,692 and 4,139,513 specify trisiloxy-hydroxyalkylmethacrylate, with the OH-group required for compatibility; DMA is not exemplified, but is claimed together with HEMA and NVP.

U.S. Pat. Nos.4,182,822 and 4,343,927 claim $C_1$-$C_4$-dialkylacrylamide hydrogel-copolymers with oligosiloxanylsilyl-alkylene methacrylates, but without exemplifying DMA copolymers.

Dimethylacrylamide (DMA) has not been used prior to this invention as the major hydrophilic monomer in silicone- and/or fluorine containing hydrogels, linear, not crosslinked copolymers of 2,2,2-trifluoroethyl methacrylate and N,N-diemthyl acrylamide are described in JP 62-115009 as a clear condensation preventing film.

It has also been discovered that DMA-copolymers with fluorinated acrylates or methacrylates with at least 5 fluorine atoms in the ester group, if prepared in the absence of a crosslinking agent, form linear clear polymers which are plasticized, but not dissolved in water. They can therefore in their water plasticized state (hydroplastic) easily be molded, coated or formed into shapes and subsequently crosslinked. This represents another practical method for manufacturing hydrogel articles.

DETAILED DESCRIPTION

The instant invention pertains to a copolymer having the characteristics of high clarity, high hydrophilicity, high oxygen permeability and which is, in the water swollen hydrated state, soft and flexible, which copolymer comprises the polymerization product of, with weight percent based on the total weight of monomers (a), (b), (c) and (d), of (a) 15-85 percent by weight of N,N-dimethylacrylamide, (b) 15-85 parts by weight of a vinyl monomer containing at least three fluorine atoms selected from the group consisting of the acrylate or methacrylate esters of formula B-1:

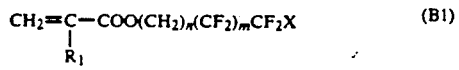

$$CH_2=C-COO(CH_2)_n(CF_2)_mCF_2X \qquad (B1)$$
$$\quad |$$
$$\quad R_1$$

wherein $R_1$ is hydrogen or methyl, n is an integer from 1-4, m is an integer from 0-11, X is hydrogen or fluorine with the proviso that, when m is 0, X is fluorine;

hexafluoroisopropyl acrylate, hexafluoroisopropyl methacrylate, undecafluoro cyclohexyl-methyl methacrylate and 2,3,4,5,6-pentafluorostyrene, (c) 0 to 50 percent by weight of a copolymerizable vinyl monomer other than the monomer of component (b), and (d) 0 to 20 percent by weight, but not more than 5 mol percent based on the combined moles of monomers (a), (b, (c) and (d), of a crosslinking agent having at least two copolymerizable vinyl groups and with the proviso, that if (d) is 0 percent, m in formula (B1) is at least 1.

Preferred copolymers are those which are the polymerization product of (a) 24.99 to 80 percent by weight of N,N-dimethylacrylamide, (b) 75 to 19.99 percent by weight of a vinyl monomer selected from the group consisting of the acrylate or methacrylate esters of formula B1 and hexafluoroisopropyl methacrylate, (c) 0 to 40 percent by weight of a copolymerizable vinyl monomer other than the monomer of component (b), and (d) 0.01 to 16 percent by weight, but not more than 4 mol percent, based on combined moles of monomers (a), (b), (c) and (d), of a crosslinking agent having at least two copolymerizable vinyl groups.

Still more preferred copolymers are those which are the polymerization product of (a) 24.9 to 70 percent by weight of N,N-dimethylacrylamide, (b) 65 to 19.9 percent by weight of a vinyl monomer selected from the group consisting of the acrylate or methacrylate esters of formula B1 and hexafluoroisopropyl methacrylate, methacrylate, (c) 10 to 40 percent by weight of a $C_1$–$C_{12}$-alkyl acrylate or methacrylate, a $C_5$–$C_{12}$ cycloalkyl acrylate or methacrylate, a $C_2$–$C_4$-hydroxy-alkyl acrylate or methacrylate, a $C_1$–$C_4$-lower alkoxy-alkyl acrylate or methacrylate, or an oligosiloxanyl-silylakyl acrylate or methacrylate containing 2 to 10 silicon atoms, and (d) 0.1 to 3 percent by weight of a crosslinking agent having at least two copolymerizable vinyl groups.

Especially preferred copolymers are those where based on the total weight of copolymer component (a) is 34.9 to 55 percent by weight, component (b) is 14.9 to 55 percent by weight, component (c) is 10 to 40 percent by weight, and component (d) is 0.1 to 2 percent by weight.

Also preferred copolymers of the instant invention are those where component (d) is 5 to 20 percent by weight.

Other preferred copolymers are those wherein component (d) is 0 percent by weight and m is at least 1.

Other preferred copolymers of the instant invention are those where component (b) is hexafluoroisopropyl methacrylate, undecafluoro-cyclohexylmethyl methacrylate or a fluorinated acrylate or methacrylate of formula B1 where X is fluorine.

Other preferred copolymers are those where component (b) is a fluorinated methacrylate of formula B1 where X is fluorine, n is 1 or 2, and m is 1 to 7, and component (c) is 10 to 40 percent by weight. Preferably in formula B1 of component (b) $R_1$ is methyl. Most preferably component (c) is methyl methacrylate or trimethylcyclohexyl methacrylate, methoxy-ethyl methacrylate, methoxy-ethyl acrylate, 2-hydroxyethyl methacrylate or mixtures thereof.

Still other preferred copolymers are those where component (b) is a fluorinated acrylate of formula B1 where X is fluorine, and component (c) is 0 percent by weight.

Other preferred copolymers of the instant invention are those where component (c) is 5 to 30 percent by weight of an oligosiloxanylsilylalkyl methacrylate having 3 to 7 silicon atoms. Most preferably component (c) is tris(trimethyl-siloxanyl-silyl)propyl methacrylate.

Still other preferred copolymers are those wherein component (c) is 0.1 to 10 percent by weight of an ethylenically unsaturated carboxylic acid, an ethylenically unsaturated sulfonic acid, tertiary di-$C_1$–$C_2$-alkylaminoalkyl acrylate or methacrylate or a hydroxy-$C_2$–$C_4$-alkyl acrylate or methacrylate.

preferred F-containing monomers are: hexafluoroisopropyl acrylate and methacrylate ($F_6$MA); heptafluoropropyl-methyl acrylate ($F_7$A) and methacrylate ($F_7$MA); nonafluorobutyl-methyl and -ethyl acrylate and methacrylate; $C_6F_{13}$-methyl and -ethyl acrylate and methacrylate $C_8F_{17}$-and $C_{10}F_{21}$ methyl- and ethyl acrylate and methacrylate. These monomers can be used alone or in combination with each other.

Most preferred are the monomers hexafluoroisopropyl methacrylate, heptafluorobutyl methacrylate and $C_6$–$C_{10}$- perfluoroalkyl-ethyl acrylate and methacrylate.

Comonomers of component (c) include a wide variety of conventional polymerizable hydrophobic and/or hydrophilic vinyl monomers, such as vinyl ($C_1$–$C_{12}$) alkyl ethers, vinyl ($C_4$–$C_{16}$) alkenoic acids, styrene, ($C_1$–$C_{12}$) alkyl, hydroxy substituted ($C_2$–$C_{12}$) alkyl, alkoxy-alkyl and polyalkoxy-alkyl and ($C_6$–$C_{12}$) mono- or bi-cycloaliphatic fumarates, maleates and especially acrylates, methacrylates, acrylamides and methacrylamides, as well as acrylic and methacrylic acid, the corresponding amino or mono- or di-(lower alkyl) amino substituted acrylic monomers; and vinyl-($C_4$–$C_7$) lactams. Typical monomers are: 2-hydroxyethyl-, 2-hydroxypropyl-, 3-hydroxypropyl acrylate and methacrylate; N-vinylpyrrolidone; N,N-dimethylaminoethyl methacrylate; methyl-, ethyl-, propyl-,isopropyl-, butyl-, sec, butyl-, tert, butyl-, cyclohexyl-, trimethylcyclohexyl-, tert, butyl cyclohexyl-, isobornyl acrylate and methacrylate; methoxyethyl-, ethoxyethyl, methoxy-ethoxy-ethyl-, ethoxy-ethoxyethyl acrylate and methacrylate, styrene; (meth)acrylamides like N,N-dimethyl-methacrylamide, N,N-diethyl(meth)acrylamide, 2-hydroxyethyl-, 2-hydroxypropyl-, 3-hydroxypropyl-acrylamide and methacrylamide; isopropyl-, n-propyl acrylamide and methacrylamide, glycidyl (meth)acrylate.

Vinyl sulfonic acid, styrene sulfonic acid and 2-methacrylamido-2methyl propane-sulfonic acid can be used in small amounts as comonomers, especially if the polymerization is carried out in solution.

Also useful as comonomers are the known oligosiloxanyl-silylalkylene(meth)acrylates with an oligosiloxy group, branched or linear, containing from 2 to 10 Si-atoms, whose terminal groups are methyl, ethyl or phenyl, for example: triphenyl-dimethyl-disiloxymethyl (meth)acrylate; pentamethyldisiloxymethyl (meth)acrylate; methyl-di(trimethylsiloxy)silyl-propylglyceryl (meth)acrylate; heptamethyl-cyclotetrasiloxymethyl (meth)acrylate; heptamethyl cyclotetrasiloxypropyl (meth)acrylate; (trimethylsilyl) decamethylpentasiloxy propyl (meth)acrylate; and tris(trimethylsiloxy) silylpropyl methacrylate.

Preferred among the other copolymerizable monomers of component (c) which can be present in amounts ranging from 0-40% are tris-(trimethylsiloxy silyl)-propyl methacrylate and alkyl methacrylates whose homopolymers have a high glass transition temperature, such as methyl-, cyclohexyl-, isopropyl-, tert-butyl-, trimethylcyclohexyl- and isobutyl methacrylate, as well as 2-hydroxyethyl methacrylate, styrene, acrylamide, and methacrylamide. Also preferred are methoxy-ethyl acrylate and methoxy-ethylmethacrylate and ethoxyethylmethacrylate.

Most preferred are methyl methacrylate, tris-(trimethyl-siloxysilyl)-propyl methacrylate and methoxyethyl methacrylate.

The crosslinking agents of component (d) which can be present in amounts up to 20% by weight are conventional polyvinyl-, typically di- or tri-vinyl-monomers, most commonly the di- or tri(meth)acrylates of dihydric or higher hydric alcohols, such as ethyleneglycol-, diethylene glycol-, triethylene glycol-, tetraethylene glycol-, propylene glycol-, butylene glycol-, hexane-1,6-diol-, thio-diethylene glycol-diacrylate and methacrylate; neopentyl glycol diacrylate; trimethylolpropane triacrylate and the like; N,N'-dihydroxyethylene-bisacrylamide and -bismethacrylamide; also diallyl compounds like diallyl phthalate and triallyl cyanurate; divinylbenzene; ethylene glycol divinyl ether. Also useful are the reaction products of hydroxyalkyl (meth)acrylates with unsaturated isocyanates, for example the reaction product of 2-hydroxyethyl methacrylate with 2-isocyanatoethyl methacrylate (IEM). This list is only examplary and not meant to be inclusive.

Also useful are polymeric crosslinking agents, like polyether-bis urethane-dimethacrylates as described in U.S. Pat. No 4,192,827 or obtained by reaction of polyethylene glycol, polypropylene glycol as polytetramethylene glycol with 2-isocyanatoethyl methacrylate (IEM) or m-isopropenyl-α,α,-dimethylbenzyl isocyanate(m-TMI), and polysiloxane-bis urethane-dimethacrylates as described in U.S. Pat. Nos. 4,486,577, and 4,605,712, and which can be present in amounts up to 20%. Also useful are the reaction products of poly(vinyl alcoohol), ethoxylated polyvinyl alcohol or of poly(vinyl alcohol-co-ethylene) with 0.1 to 10 mol % vinyl isocyanates like IEM or m-TMI.

Preferred crosslinking agents are ethylene glycol dimethacrylate, diethylene glycol dimethacrylate, 1,4-butaediol di(meth)acrylate neopentyl glycol diacrylate; and poly(vinyl alcohol-co-ethylene) reacted with 1-10 mol % 2-isocyanatoethyl methacrylate, most preferred is ethylene glycol dimethacrylate.

When present, component (d) is preferably present in an amount of at least 0.01parts by weight, based on the total weight of the comonomer mixture.

The copolymers of this invention are clear hydrophilic and highly oxygen permeable. They can swell in water to form hydrogels with 25 to 75% water and are useful in a variety of applications, such as gas separation membranes or as oxygen permeable wound dressings or bandages; Due to their clarity and high oxygen permeability they are especially suited for ophthalmic devices such as soft contact lenses useful for daily or extended wear. They are also useful as carriers for the controlled delivery of drugs either as dermal patches, orally taken beads, body implants or eye inserts.

Synthesis

The novel polymers are prepared by free-radical polymerization either in bulk or in solution and using heat- or UV-activated initiators. Typical heat activated initiators are preferably peroxides or azo catalysts having a half-life at the polymerization temperature of at least 20 minutes. Typical useful peroxy compounds include: isopropyl percarbonate, tert-butyl peroctoate, benzoyl peroxide, lauroyl peroxide, decanoyl peroxide, acetyl peroxide, succinic acid peroxide, methyl ethyl ketone peroxide, tert+-butyl peroxyacetate, propionyl peroxide, 2,4-dichlorobenzoyl peroxide, tert.-butyl peroxypivalate, pelargonyl peroxide, 2,5-dimethyl-2,5-bis(2-ethylhexanoyl-peroxy)hexane, p-chlorobenzoyl peroxide, tert-butyl peroxybutyrate, tert-butyl peroxymaleic acid, tert-butyl-peroxyisopropyl carbonate, bis(1-hydroxy-cyclohexyl)peroxide; azo compounds include: 2,2'-azo-bis-isobutyronitrile; 2,2'-azo-bis(2,-4dimethylvaleronitrile); 1,1'-azo-bis (cyclohexane carbonitrile). 2,2'azo-bis(2,4-dimethyl-4-methoxyvaleronitrile).

Other free radical generating mechanisms can be employed such as X-rays electron-beams and UV-radiation. Preparation of contact-lens blanks by UV radiation in the presence of a photoinitiator such as diethoxyacetophenone, 1-hydroxycyclohexyl phenyl ketone, 2,2-dimethoxy-2-phenylacetophenone, phenothiazine. diisopropylxanthogen disulfide benzoin, benzoin methyl ether and other benzoin derivatives is a preferred method.

The novel copolymers can be prepared in form of sheets or films by casting the monomer solutions in the appropriate molds or by casting a film with a knife- or roller coater and subsequently carrying out the polymerization either using UV or heat. It is also possible to prepare the polymers in form of round beads of 0.01to 2.0 mm diameter by suspension polymerization in aqueous brine, as f.i. described in U.S. Pat. Nos. 4,224,427.

The polymers can be fabricated into any desired shape such as contact lenses by direct molding or by spin-casting either in bulk or in the presence of a solvent.

For contact-lens manufacture, the polymer is usually prepared in shape of a rod, button or sheet or some other desired shape by exposing the closed and filled mold to heat, typically throughout a 3-24 hour cycle of increasing temperatures, from 30°-120°C. The finished article can subsequently be further shaped during cutting and polishing steps. For use as a contact lens, the polymer is preferably crosslinked. In the absence of a crosslinking agent, the resulting polymer is soluble or plasticizable in solvents and can be used as a coating or be thermo-formed.

The polymerization can also be carried out in solvents, with or without a polyvinyl-crosslinking agent. Typical solvents include alcohols such as methanol, ethanol, isopropanol, butanol and tert-butanol; esters such as isopropyl acetate; acetone, methyl ethyl ketone, methyl propyl ketone, methyl isopropyl ketone, cyclohexanone and other ketones; N,N-dimethylformamide, N,N-dimethylacetamide, N-methylpyrrolidone, dimethyl sulfoxide; ethers such as ethoxy-, methoxy- and butoxy-ethanol; ethylene glycol dimethyl- and diethyl ether; methoxyethyl acetate; ethylene- and propylene carbonate;

Solution polymerizations are carried out in an inert atmosphere at temperatures between 30° and 80° C., dependent on initiator and solvent, for 3-24 hours. The polymer solutions can be used directly to form coatings which can subsequently be crosslinked if a suitable reactive group has been built into the polymer such as a UV-reactive group or an epoxy group.

Freshly distilled monomers are used for all experiments in the working Examples. Tris(trimethylsiloxysilyl)-propyl methacrylate ($Si_4MA$) is obtained from Shin-Etsu Corporation; perfluoroalkyl-ethyl acrylates ($R_fA$ and methacrylate ($R_fMA$) are obtained from American Hoechst Corporation with the following average $R_f$-chain-length distribution. $C_6F_{12} < 5\%$; $C_8F_{17}$ about 60%; $C_{10}F_{21}$ about 25% $C_{12}F_{25}$ about 10%. All other monomers are obtained from commercial supply houses (N,N-dimethylacrylamide=DMA; ethylene glycol dimethacrylate EGDMA; methyl methacrylate=MMA).

In the following examples, water content is expressed as:

$$H_2O\ (\%) = \frac{\text{Water swollen sample (g)} - \text{dry sample (g)}}{\text{water swollen sample (g)}}$$

Physical-mechanical measurements are carried out on an INSTRON testing machine, model 1123.

Oxygen permeability measurements are carried out using a CREATECH Permeometer model 201T, in air, and are expressed as $$O_2.DK = \frac{cm^2(STP) \times cm}{cm^3 \cdot sec.cmHg} \times 10^{10}\ \text{(barrers)}$$

EXAMPLE 1

5 g (N,N-Dimethacrylamide (DMA), 4.95 g heptafluorobutyl methacrylate and 0.05 g ethylene glycol dimethacrylate (FGDMA) are mixed together with 0.02 g benzoin methyl ether (BME). The mixture is degassed, kept under dry nitrogen and with a pipette filled into round polypropylene button molds having a height of 10 mm and a 12 mm diameter. The mold is capped with a polypropylene cap and the filled mods are set into a tray and exposed to UV-radiation from a SYLVANIA BlackLite-Blue lamp while sparging the UV-radiation box with dry nitrogen, first only from below for 2 hours, followed by another hour from top and bottom. The finished buttons are tempered for 1 hour at 110° C., cooled to room temperature and pulled out of the mold.

From one of the clear, hard buttons a 0.25 mm slice is cut off for oxygen permeability measurements after equilibration in water, and a thicker, ~2 mm slice is cut off for swelling measurements.

The remainder of the button is used to determine dry Shore-D hardness and, after 1 week equllibration in water, wet Shore-A hardness.

The polymer prepared above had a Shore-D hardness (dry) of 87, a Shore-A hardness of 15, a water content ($H_2O$, % by weight) of 58 and an $O_2.DK$ of 30 barrers.

For comparison, a poly-(2-hydroxyethyl methacrylate) hydrogel has a water content of 39% and an $O_2.DK$ of 6.5 barrers.

EXAMPLE 2-6

The procedure of Example 1 is repeated with 10 g each of the monomer compositions listed below and the properties of the clear copolymers are determined.

| | Composition[1] (% by Weight) | | | | Shore Hardness | | |
|---|---|---|---|---|---|---|---|
| Ex. No. | DMA | $F_7MA$ | EGDMA | $H_2O$ % | Dry D | Wet A | $O_2.DK$ barrers |
| 1 | 50 | 49.9 | 0.1 | 58 | 87 | 15 | 30 |
| 2 | 50 | 49.5 | 0.5 | 48 | 85 | 20 | 28 |
| 3 | 48 | 51.8 | 0.2 | 47 | 85 | 25 | 25 |
| 4 | 47 | 52.8 | 0.2 | 46 | 85 | 30 | 24 |
| 5 | 45 | 54.8 | 0.2 | 47 | 86 | 42 | 22 |
| 6 | 40 | 58.8 | 0.2 | 32 | 85 | 75 | — |

[1]$F_7MA$: heptafluorobutyl methacrylate
EGDMA: ethylene glycol dimethacrylate

EXAMPLES 7-18

The procedure of Example 1 is repeated with 10 g of the monomer mixtures listed below. All copolymers are clear and their properties are listed below.

| | Composition[1] (% by Weight) | | | | | Shore Hardness | | |
|---|---|---|---|---|---|---|---|---|
| Ex. No. | DMA | $Si_4MA$ | $F_nMA$ (n) | EGDMA | $H_2O$ % | Dry D | Wet A | $O_2.DK$ barrers |
| 7 | 50 | 30 | 19.5(7) | 0.5 | 49 | 82 | 36 | 28 |
| 8 | 50 | 20 | 29.8(7) | 0.2 | 57 | 84 | 23 | 41 |
| 9 | 45 | 25 | 29.8(7) | 0.2 | 43 | 82 | 32 | 37 |
| 10 | 45 | 15 | 39.8(7) | 0.2 | 47 | 84 | 25 | 33 |
| 11 | 40 | 40 | 19.8(7) | 0.2 | 42 | 78 | 50 | 39 |

-continued

| Ex. No. | Composition[1] (% by Weight) | | | | $H_2O$ % | Shore Hardness | | $O_2$·DK barrers |
|---|---|---|---|---|---|---|---|---|
| | DMA | Si$_4$MA | F$_n$MA (n) | EGDMA | | Dry D | Wet A | |
| 12 | 40 | 30 | 29.8(7) | 0.2 | 43 | 80 | 40 | 30 |
| 13 | 40 | 25 | 34.8(7) | 0.2 | 40 | 82 | 39 | 36 |
| 14 | 40 | 40 | 19.8(6) | 0.2 | 31 | 80 | 45 | 32 |
| 15 | 40 | 30 | 29.8(6) | 0.2 | 34 | 80 | 79 | 21 |
| 16 | 45 | 35 | 19.8(6) | 0.2 | 47 | 81 | 32 | 39 |
| 17 | 47 | 33 | 19.8(6) | 0.2 | 48 | 82 | 30 | 38 |
| 18 | 50 | 30 | 19.8(6) | 0.2 | 50 | 83 | 21 | 37 |

[1] F$_n$MA with n = 7: heptafluorobutyl methacrylate
F$_n$MA with n = 6: hexafluoroisopropyl methacrylate
Si$_4$MA: tris-(trimethylsiloxanyl-silyl)-propyl methacrylate
EGDMA: ethylene glycol dimethacrylate

EXAMPLE 19

The procedure of Example 1 is repeated, using 5 g DMA, 4.95. g pentafluorostyrene and 0.05 g EGDMA. A clear, hard polymer is obtained (Shore-D=85) which absorbs 22% by weight of water and has an $O_2$-DK of 6 barrers.

EXAMPLES 20-21

Using the procedure of Example 1, clear copolymers of DMA with Si$_4$MA[1] and R$_f$A[1] are prepared, having the compositions and properties listed below:

| Ex. | Composition[1] (% by weight with 0.2% EGDMA) | | | $H_2O$ % | Shore Hardness | | $O_2$·DK (barrers) |
|---|---|---|---|---|---|---|---|
| | DMA | R$_f$—A | Si$_4$MA | | D Dry | A Wet | |
| 20 | 50 | 49.8 | — | 48 | 82 | 24 | 26 |
| 21 | 50 | 19.8 | 30 | 47 | 80 | 15 | 32 |

[1] R$_f$A = C$_n$F$_{2n+1}$CH$_2$CH$_2$OC(=O)—CH=CH$_2$ with
n = 6/8/10/12 in ratios of 5/60/25/10 (% by weight)
Si$_4$MA: tris-(trimethylsiloxanyl-silyl)-propyl methacrylate The polymer buttons of Example 20 are easily by machining and polishing and equilibration in water fabricated into contact lenses.

In contrast to Ex. 20, mixtures of either 50% N-vinylpyrrollidone or of N-vinylacetamide with 50% R$_f$A are found to be completely immiscible, even in the monomeric state.

EXAMPLES 22-30

With the monomer solutions of the Examples listed in the table below, flat polymer sheets are prepared by pouring the mixtures containing 0.1% by weight BME as initiator into glass molds lined with clear MYLAR sheets and using 0.5 mm silicone-cord as spacer, held together by spring clamps. The molds are exposed to UV radiation for 4 hours, followed by 1 hour annealing at 100° C. The clear sheets are swollen in water and their physical-mechanical properties determined on an INSTRON testing machine, model 1123.

A separate fraction of the mixtures described above is used to fill polypropylene contact lens molds and cured by UV as described. The resulting contact lenses are, clear, wettable and optically flawless after equilibration in water.

| Ex. No. | Polymer of Ex. No. | Composition (% by Weight) | | | $H_2O$ % | INSTRON-data | | |
|---|---|---|---|---|---|---|---|---|
| | | DMA | Si$_4$MA | F$_n$MA[1] (0.2% or 0.5% EGDMA) | | Tensile St. Kg/cm$^2$ | Youngs Mod. Kg/cm$^2$ | Elongation % |
| | | | | F$_n$MA n = 7 | | | | |
| 22 | 5 | 45 | — | 54.8 | 47 | 13.3 | 22.3 | 455 |
| 23 | 4 | 47 | — | 52.8 | 46 | 13.9 | 9.8 | 425 |
| 24 | 3 | 48 | — | 51.8 | 47 | 11.9 | 5.8 | 455 |
| 25 | 2 | 50 | — | 49.5 | 48 | 15.7 | 10.2 | 264 |
| 26 | 7 | 50 | 30 | 19.5 | 49 | 7.0 | 6.8 | 182 |
| | | | | F$_n$MA n = 6 | | | | |
| 27 | 16 | 45 | 35 | 19.8 | 47 | 10.3 | 23.1 | 469 |
| 28 | 17 | 47 | 33 | 19.8 | 48 | 14.2 | 10.7 | 459 |
| | | | | R$_f$A n = 13-21 | | | | |
| 29 | 20 | 50 | — | 49.8 | 48 | 13.8 | 10.2 | 478 |
| 30 | 21 | 50 | 30 | 19.8 | 47 | 6.9 | 2.2 | 622 |

[1] F$_n$MA: n = 7: heptafluorobutyl methacrylate
n = 6: hexafluorisopropyl methacrylate
R$_f$A: R$_f$-ethylene acrylate with R$_f$-chain length distribution given in Ex. 20-21.

EXAMPLES 31-32

Synthesis of linear, water plasticized fluorinated hydroplastic.

EXAMPLE 31

5 g F$_7$MA and 5 g DMA are dissolved in 10 g ethanol together with 0.02 g 2,2'-azo-bis(2,4-dimethylvaleronitrile)(VAZO-52) and stirred under nitrogen in a bottle on a constant-temperature bath for 24 hours. The resultant viscous solution is dried to yield 10 g of a clear copolymer which equilibrated in distilled water to a viscous hydroplastic with 48% by weight of $H_2O$.

EXAMPLE 32

The same procedure of Example 31 is repeated, using 10 g $R_fA$ with the structure and $R_f$-chain length distribution given in Example 20, 10 g DMA, 1 g dodecylthiol, 10 g ethanol and 5 g methyl ethyl ketone, MEK. A highly viscous syrup is obtained which on equilibration in excess water gives a low viscosity hydroplastic with 55% by weight of $H_2O$.

EXAMPLES 33-34

Synthesis of hydrogels by casting with a solvent 4.25 g Heptafluorobutyl methacrylate ($F_7MA$), 4.25 g DMA and 1.5 g poly(ethylene-co-vinylalcohol) (EVA) (32 mol % ethylene, 28,000 MW), which had previously been reacted as a 10% solution in N-methylpyrrolidone with 5 mol % isocyanatoethyl methacrylate (EVA-IEM), are dissolved by stirring in N-methylpyrrolidone to make a 50% solution. 0.1 g Benzoin methyl ether is added and dissolved. The mixture is degassed, sparged with dry nitrogen and poured into a mold (0.5 mm spaces between Mylar lined glass plates), followed by exposure to UV for 12 hours. The clear sheet is removed, equilibrated in distilled water until all N-methylpyrrolidone is extracted, and tested as described.

The same procedure is repeated, but using as comonomers a mixture of equal parts tris-(trimethylsiloxanyl silyl)-propyl methacrylate ($Si_4MA$) and $F_7MA$.

The clear polymers have the following properties:

| Ex. No. | DMA | Composition (% by weight) F$_7$MA | Si$_4$MA | EVA-IEM | H$_2$O (%) | O$_2$.DK barrers |
|---|---|---|---|---|---|---|
| 33 | 41 | 41 | — | 18 | 39 | 13 |
| 34 | 41 | 20.5 | 20.5 | 18 | 39 | 23 |

A separate fraction of the mixtures described above is used to fill polypropylene contact lens molds and cured by UV as described. The resulting contact lenses are clear, wettable and optically flawless after equilibration in water.

EXAMPLE 35A AND 35B

Synthesis of anionic and amphoteric hydrogels.

Using the same procedure as described in Examples 33 and 34, two hydrogels are synthesized using a comonomers 2-methacrylamido-2-methyl propane-sulfonic acid (AMPS) and N,N-dimethylaminoethyl methacrylate (DAMA). The polymer compositions and their equilibrium water contents are shown below.

| Ex. No. | DMA | F$_7$MA | EVA-IEM | AMPS | DAMA | H$_2$O % |
|---|---|---|---|---|---|---|
| 35a | 44.3 | 37.6 | 13.4 | 4.7 | — | 63 |
| 35b | 44.3 | 37.6 | 13.4 | 2.7 | 2.0 | 46 |

EXAMPLE 36-37

Using the procedure of Example 1, the following compositions are synthesized and tested.

| Ex. | DMA | Composition (% by weight) R$_f$A$^{(1)}$ | EGDMA | Shore D Dry | Shore A Wet | H$_2$O % | O$_2$.DK barrers |
|---|---|---|---|---|---|---|---|
| 36 | 50 | n = 8 49.8 | 0.2 | 82 | 26 | 48.7 | 26.4 |
| 37 | 50 | n = 6-12 49.8 | 0.2 | 82 | 26 | 48.47 | 26.0 |

(1) n = 8: $C_8F_{17}$—$CH_2CH_2$ acrylate
n = 6-12: $R_f$-distribution shown in Example 20

Both polymers are water clear in the dry and water swollen state.

EXAMPLES 38-49

Use of $R_f$-ethylene methacrylates as comonomers.

The compositions listed in the following table are synthesized in form of buttons and as 0.5 mm thick sheets, as described in Examples 1 and 22-30. The buttons are used to measure hardness and oxygen permeability, and the sheets for testing mechanical-physical properties.

All polymers, except where noted, are clear in the water swollen state.

Examples 38-49

| Ex. No. | DMA | R$_f$MA | Composition[1] Si$_4$MA | MMA (% by weight) | XL | Shore D Hardness | H$_2$O % | INSTRON Data[2] T.S. (kg/cm$^2$) | Y.M. (kg/cm$^2$) | Elongation % | O$_2$.DK barrers |
|---|---|---|---|---|---|---|---|---|---|---|---|
| 38 | 50 | 49.5 | — | — | 0.2 | 78 | 55.8 | polymers are opaque | | | |
| 39 | 40 | 49.8 | — | 10 | 0.2 | 83 | 47.9 | polymers are opaque | | | |
| 40 | 50 | 24.9 | — | 24.9 | 0.2 | 86 | 63.2 | 10.4 | 4.7 | 440 | 26.6 |
| 41 | 45 | 29.8 | — | 25 | 0.2 | 85 | 56.6 | 13.5 | 6.5 | 430 | 21.7 |
| 42 | 45 | 34.8 | — | 20 | 0.2 | 84 | 56.6 | 13.2 | 6.7 | 420 | 22.7 |
| 43 | 40 | 39.8 | — | 20 | 0.2 | 84 | 49.4 | 19.3 | 9.2 | 420 | 19.1 |
| 44 | 40 | 44.8 | — | 15 | 0.2 | 83 | 48.2 | 18.6 | 10.1 | 415 | 26.1 |
| 45 | 40 | 49.8 | 10 | — | 0.2 | 78 | 45.7 | - polymer is opaque | | | |
| 46 | 40 | 39.8 | 10 | 10 | 0.2 | 81 | 48.1 | 12.4 | 5.2 | 460 | 27.0 |
| 47 | 40 | 34.8 | 15 | 10 | 0.2 | 82 | 47.0 | 11.1 | 4.0 | 515 | 30.2 |
| 48 | 50 | 24.0 | 12.9 | 12.9 | 0.2 | 82 | 60.7 | 6.6 | 13.4 | 620 | 35.6 |

Examples 38-49-continued

| Ex. No. | DMA | R_fMA | Composition[1] Si_4MA MMA (% by weight) | | XL | Shore D Hardness | H_2O % | INSTRON Data[2] T.S. Y.M. (kg/cm²) | | Elongation % | O_2.DK barrers |
|---|---|---|---|---|---|---|---|---|---|---|---|
| 49 | 45 | 34.8 | 10 | 10 | 0.2 | 82 | 54.4 | 11.4 | 4.1 | 460 | 28.2 |

[1]R_fMA: 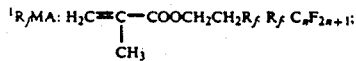 R_f C_nF_{2n+1};

n = 6/8/10/12 = in ratios of 0.2/70.3/26.0/1.6 (% by weight)

Si_4MA: 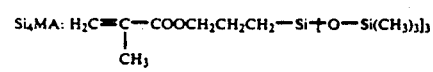

XL: ethylene glycol dimethacrylate
[2]TS: Tensile Strength
YM: Young's Modulus

EXAMPLES 50-53

Hydrogels with increased crosslink density and other comonomers.

The polymers listed in the following table are synthesized in form of buttons and 0.5 mm thick sheets, and their swelling and physico-mechanical properties are determined, as described in Examples 1 and 22-30.

| Ex. | DMA | Composition[1] R_fMA MMA TMMA (% by weight) | | | XL | Shore D (dry) | H_2O % | Shore A (Wet) | O_2.DK barrers |
|---|---|---|---|---|---|---|---|---|---|
| 50 | 50 | 24.75 | 24.75 | — | 0.5 | 85 | 58.3 | 33 | 24.2 |
| 51 | 50 | 24.5 | 24.5 | — | 1.0 | 86 | 54.7 | 43 | 22.1 |
| 52 | 50 | 24.0 | 24.0 | — | 2.0 | 86 | 49.5 | 57 | 21.6 |
| 53 | 45 | 34.8 | — | 20 | 0.2 | 83 | 46.6 | 45 | 28.1 |

[1]DMA: N,N-dimethylacrylamide
R_fMA: as described in Examples 38-49
MMA: methyl methacrylate
TMMA: trimethyl cyclohexyl methacrylate
XL: ethylene glycol dimethacrylate

EXAMPLE 54

5 g N,N-Dimethylacrylamide, 3.98 g R_f-ethyl acrylate with the R_f-chain length distribution shown in Example 20, 1.0 g 2-hydroxyethyl methacrylate, 0.02 g ethylene glycol dimethacrylate and 0.02 g benzoin methyl ether are mixed together degassed in vacuo and sparged with dry nitrogen; the mixture is filled into a MYLAR lined glass mold using 0.5 mm silicone cord as spacer. The mold is exposed to UV radiation from a SYLVANIA BlackLite-Blue Lamp for 5 hours, after which it is taken apart. The clear polymer sheet is equilibrated in water; it is tough, strong and resilient, with a water content of 60% and a oxygen permeability, O_2.DK of 32 barrers.

EXAMPLE 55-57

40 g N,N-Dimethylacrylamide, 24.75 g C_6F_{13}CH_2CH_2-methacrylate, 10.00 g 2-hydroxyethyl methacrylate, 0.5 g ethylene glycol dimethacrylate and 24.75 g of an alkoxy-ethyl acrylate or methacrylate (M-4) as listed in the table are mixed, together with 0.2 g benzoin methyl ether. Buttons are prepared in molds as described in Example 1 and tested. The results are shown in the table.

| Ex. No. | M-4 | Shore-D Hardness | H_2O % | T.S. (kg/cm²) | Y.M. | El. % | O_2.DK barrers |
|---|---|---|---|---|---|---|---|
| 55 | MOMA[1] | 84 | 59 | 3.5 | 2.2 | 187 | 24 |
| 56 | MOA[2] | 80 | 64 | 3.5 | 2.0 | 198 | 28 |
| 57 | EOMA[3] | 83 | 57 | 7.8 | 1.8 | 190 | 22 |

[1]methoxy-ethyl methacrylate
[2]methoxy-ethyl acrylate
[3]ethoxy-ethyl methacrylate

EXAMPLE 58

A polymer button prepared in Example 55 is cut and polished in form of a contact lens, and subsequently equilibrated in phosphate buffered saline solution, resulting in a 14.5 mm diameter, oxygen permeable soft contact lens.

What is claimed is:

1. A hydrated composition in form of a contact lens which comprises a copolymer, having the characteristics of high clarity, high oxygen permeability and which is, in the water swollen hydrated state, soft and flexible, which copolymer comprises the polymerization product of, with weight percent based on the total weight of monomers (a), (b), (c) and (d), of
   (a) 24.9 to 70 percent by weight of N,N-dimethylacrylamide,
   (b) 65 to 19.9 percent by weight of a vinyl monomer selected from the group consisting of the acrylate or methacrylate esters of formula B1

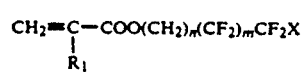 (B1)

wherein
R_1 is hydrogen or methyl,
n is an integer from 1-4,
m is an integer from 0-11, X is hydrogen or fluorine, with the proviso that, when m is 0, X is fluorine, and hexafluoroisopropyl methacrylate, (c) 10 to 40 percent by weight of a $C_2$–$C_4$-hydroxyalkyl acrylate or methacrylate, a $C_2$–$C_4$-alkoxy-alkyl acrylate or methacrylate or an oligosiloxanyl-silylalkyl acrylate or methacrylate containing 2 to 10 silicon atoms, or mixture thereof, and (d) 0.1 to 3 percent by weight of a crosslinking agent having at least two copolymerizable vinyl groups.

2. A composition according to claim 1 where in the copolymer, component (c) is methoxy-ethyl methacrylate, methoxy-ethyl acrylate or ethoxy-ethyl methacrylate.

3. A composition according to claim 1 where in the copolymer, component (b) is hexafluoroisopropyl methacrylate, undecafluorocyclohexyl-methyl methacrylate or a fluorinated acrylate or methacrylate of formula B1 where X is fluorine.

4. A composition according to claim 1 where in the copolymer, component (b) is a fluorinated methacrylate of formula B1 where X is fluorine, n is 1 or 2, and m is 1 to 7.

5. A composition according to claim 1 where in the copolymer, component (b) $R_1$ is methyl.

6. A composition according to claim 1 where in the copolymer, component (c) is methoxy-ethyl acrylate, ethoxy-ethyl methacrylate, methoxy-ethyl methacrylate, 2-hydroxyethyl methacrylate or a mixture thereof.

7. A composition according to claim 1 where in the copolymer, component (c) is methoxy-ethyl methacrylate or a mixture of methoxy-ethyl methacrylate and 2-hydroxyethyl methacrylate.

8. A composition according to claim 1 where in the copolymer, component (c) is 5 to 30 percent by weight of an oligosiloxanyl-silylalkyl methacrylate having 3 to 7 silicon atoms.

9. A composition according to claim 1 wherein component (c) is tris(trimethylsiloxanyl-silyl)propyl methacrylate.

10. A composition according to claim 1 where in the copolymer, component (d) is a poly(vinyl alcohol-co-ethylene) reacted with 0.1–10 mol % of a vinyl unsaturated isocyanate.

11. A composition according to claim 1 where in the copolymer, component (c) is 0.1 to 10 percent by weight of an ethylenically unsaturated carboxylic acid, an ethylenically unsaturated sulfonic acid, a tertiary di-$C_1$–$C_2$-alkylaminoalkyl acrylate or methacrylate or a hydroxy-$C_2$–$C_4$-alkyl acrylate or methacrylate.

12. A hydrated composition in form of an ophthalmic prosthetic device which comprises a copolymer, having the characteristics of high clarity, high hydrophilicity, and high oxygen permeability and which is, in the water swollen hydrated state, soft and flexible, which copolymer comprises the polymerization product of, with weight percent based on the total weight of monomers (a), (b), (c) and (d), of (a) 15–85 percent by weight of N,N-dimethylacrylamide, (b) 15–85 parts by weight of a vinyl monomer containing at least three fluorine atoms selected from the group consisting of the acrylate or methacrylate esters of formula B1

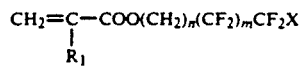

wherein
$R_1$ is hydrogen or methyl,
n is an integer from 1–4,
m is an integer from 0–11,
X is hydrogen or fluorine, with the proviso that, when m is 0, X is fluorine;
hexafluoroisopropyl acrylate, hexafluoroisopropyl methacrylate undecafluorocyclohexyl-methylmethacrylate and 2,3,4,5,6-pentafluorostyrene, (c) 0 to 50 percent by weight of a copolymerizable vinyl monomer other than the monomer of component (b), and (d) 0 to 20 percent by weight, but not more than 5 mol percent based on the combined moles of monomers (a), (b), (c) and (d), of a crosslinking agent having at least two copolymerizable vinyl groups; with the proviso, that if (d) is 0 percent, m in formula (B1) is at least 1.

13. A hydrated composition in form of a bandage which comprises a copolymer, having the characteristics of high clarity, high hydrophilicity, and high oxygen permeability and which is, in the water swollen hydrated state, soft and flexible, which copolymer comprises the polymerization product of, with weight percent based on the total weight of monomers (a), (b), (c) and (d), of (a) 15–85 percent by weight of N,N-dimethylacrylamide, (b) 15–85 parts by weight of a vinyl monomer containing at least three fluorine atoms selected from the group consisting of the acrylate or methacrylate esters of formula B1

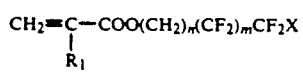

wherein
$R_1$ is hydrogen or methyl,
n is an integer from 1–4,
m is an integer from 0–11,
X is hydrogen or fluorine, with the proviso that, when m is 0, X is fluorine;
hexafluoroisopropyl acrylate, hexafluoroisopropyl methacrylate undecafluorocyclohexyl-methylmethacrylate and 2,3,4,5,6-pentafluorostyrene, (c) 0 to 50 percent by weight of a copolymerizable vinyl monomer other than the monomer of component (b), and (d) 0 to 20 percent by weight, but not more than 5 mol percent based on the combined moles of monomers (a), (b), (c) and (d), of a crosslinking agent having at least two copolymerizable vinyl groups; with the proviso, that if (d) is 0 percent, m in formula (B1) is at least 1.

14. A hydrated composition in form of a drug delivery device which comprises a copolymer, having the characteristics of high clarity, high hydrophilicity, and high oxygen permeability and which is, in the water swollen hydrated state, soft and flexible, which copolymer comprises the polymerization product of, with weight percent based on the total weight of monomers (a), (b), (c) and (d), of (a) 15-85 percent by weight of N,N-dimethylacrylamide, (b) 15-85 parts by weight of a vinyl monomer containing at least three fluorine atoms selected from the group consisting of the acrylate or methacrylate esters of formula B1

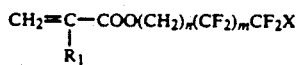  (B1)

wherein
$R_1$ is hydrogen or methyl,
n is an integer from 1-4,
m is an integer from 0-11,
X is hydrogen or fluorine, with the proviso that, when m is 0, X is fluorine;
hexafluoroisopropyl acrylate, hexafluoroisopropyl methacrylate undecafluorocyclohexyl-methylmethacrylate and 2,3,4,5,6-pentafluorostyrene, (c) 0 to 50 percent by weight of a copolymerizable vinyl monomer other than the monomer of component (b), and (d) 0 to 20 percent by weight, but not more than 5 mol percent based on the combined moles of monomers (a), (b), (c) and (d), of a crosslinking agent having at least two copolymerizable vinyl groups; with the proviso, that if (d) is 0 percent, m in formula (B1) is at least 1.

* * * * *